United States Patent [19]

Munari

[11] Patent Number: 4,976,750

[45] Date of Patent: Dec. 11, 1990

[54] METHOD AND DEVICE FOR THE CONTROL OF GAS CHROMATOGRAPHIC FUNCTIONS

[75] Inventor: Fausto Munari, Milan, Italy

[73] Assignee: Carlo Erba Strumentazione S.p.A., Italy

[21] Appl. No.: 394,004

[22] Filed: Aug. 15, 1989

[30] Foreign Application Priority Data

Aug. 22, 1988 [IT] Italy .................. 21728 A/88

[51] Int. Cl.$^5$ ............................. B01D 15/08
[52] U.S. Cl. ............................. 55/21; 55/67; 55/197; 55/386
[58] Field of Search .............. 55/21, 67, 197, 386

[56] References Cited

U.S. PATENT DOCUMENTS

| | | | |
|---|---|---|---|
| 2,875,606 | 3/1959 | Robinson | 55/67 X |
| 3,250,057 | 5/1966 | Clarke | 55/67 |
| 3,422,665 | 1/1969 | Haase | 55/67 X |
| 3,494,104 | 2/1970 | Royer | 55/67 |
| 3,496,702 | 2/1970 | Carel et al. | 55/67 |
| 3,712,028 | 1/1973 | Deans | 55/67 |
| 4,271,697 | 6/1981 | Mowery, Jr. | 55/67 X |
| 4,442,217 | 4/1984 | Deans | 55/386 X |
| 4,728,344 | 3/1988 | Stacy | 55/67 |
| 4,774,190 | 9/1988 | Weiss | 55/67 X |
| 4,805,441 | 2/1989 | Sides et al. | 55/67 X |
| 4,814,089 | 3/1989 | Kumar | 55/67 X |
| 4,824,446 | 4/1989 | Mowery, Jr. | 55/67 |
| 4,861,488 | 8/1989 | Kenney et al. | 55/67 X |

FOREIGN PATENT DOCUMENTS

| | | | |
|---|---|---|---|
| 1299684 | 6/1962 | France | 55/67 |
| 1214627 | 12/1970 | United Kingdom | 55/67 |

OTHER PUBLICATIONS

Pacciarelli, *Proc. 8th Int. Symp. Capillary Chromatography*, Riva del Garda (Huthig, Heidelberg, 1987), pp. 1204–1215.

Primary Examiner—Robert Spitzer
Attorney, Agent, or Firm—Lerner, David, Littenberg, Krumholz & Mentlik

[57] ABSTRACT

The functions of a gas chromatograph depending on the advancement stage of the analysis can be at least partly controlled by detecting the data relating to the carrier feeding conditions (pressure and/or flow) in a position upstream the injection point of the sample to be analyzed, and by measuring the variations occurring in the conditions after the sample injection. This method is particularly convenient for the analysis of samples with high volumes of eluent, and one of its preferred embodiments foresees the use of a pressure sensor in a point of the carrier feeding duct or, alternatively, of a flow sensor positioned between two points of the feeding duct.

16 Claims, 3 Drawing Sheets

METHOD AND DEVICE FOR THE CONTROL OF GAS CHROMATOGRAPHIC FUNCTIONS

BACKGROUND OF THE INVENTION

1. Field of the Invention

The present invention relates to a method and a device to control those functions of a gas chromatograph which depend on the advancement stage of a sample analysis, and particularly the functions which can be correlated to the presence of eluent in the separation column or in the precolumn.

2. Description of the Prior Art

As it is known, in a gas chromatographic analysis a number of the gas chromatograph functions depend on the advancement stage of the analysis itself. Examples of said functions are the on/off switching of valves in an HPLC/GC interface of the so-called "loop" type, switching which depends on the sample complete introduction; or the rise of the oven temperature after the eluent complete evaporation in analyses using a precolumn (retention gap).

Another example, the following description will refer to, is represented by the commutation of the regulating valves of an exhaust duct, or splitter, mounted on a point whatsoever of the sample elution run, between the injector and the detector, in a gas chromatograph used to analyze large volumes of samples (e.g., samples containing up to several ml of eluent). As it is known, in said analyses the splitter has the function of avoiding that the whole considerable amount of eluent (solvent, supercritical fluid or the like) flows through the column and/or the detector, discharging most of it before arriving, while only a small fraction of same is actually sent to the analysis or the detector.

Obviously, once the eluent has passed, all (or almost) the remaining part of the sample, which in the meantime has started to elute, will be sent to the detector and its components analyzed: a switching valve working on the splitter is provided for this purpose. Of course, before operating said valve, it is necessary to ensure the eluent has practically all passed through the precolumn or column, which can be done only by monitoring the solvent peak on the detector during the first part of the injection, or by performing a test injection and determining how long the solvent takes to elute completely. If the volume of the injected sample varies, said test injection must be repeated, in that the solvent elution time varies as well. Anyhow, in both cases, the time the operator requires for said controls is too long. Furthermore the time necessary for said operations is never exactly the same; if for instance it is considered the time elapsed between the sample injection and the eluent complete evaporation, it can be noticed that said time is conditioned by a lot of factors which render the moment of evaporation end not reproducible with sufficient precision. Similar problems arise in the other aforementioned examples of the gas chromatograph controllable functions. There is therefore the need to automate the control of those gas chromatographic functions which depend on the advancement stage of the analysis itself, but which cannot be precisely correlated to the time elapsed from the beginning of the analysis.

OBJECTS OF THE INVENTION

An object of the present invention is to solve the aforementioned problems by providing a method for the automatic control of the functions of a gas chromatograph which depend on the analysis advancement stage. A second object of the invention is to provide a device to automatically or semi-automatically control the functions of a gas chromatograph which depend on the advancement stage of the analysis.

SUMMARY OF THE INVENTION

These and other objects are achieved by the method and the device provided by the invention, which allow to automatically control, thanks to a feedback effect, said functions of a gas chromatograph in an easy, reliable and economic way. More in particular, the present invention relates to a method for the control of one or more functions of a gas chromatograph which depend on the advancement stage of the gas chromatographic analysis, characterized by the fact of utilizing for said controls the variations in the parameters of carrier gas feeding (pressure and/or flow) upstream of the injection point of the sample to be analyzed, as caused by the presence of said sample. Moreover the invention relates to a device for the control of at least one of the functions of a gas chromatograph which depend on the advancement stage of a gas chromatographic analysis, characterized in that it comprises: means to detect the data relating to the parameters of the carrier gas feeding (pressure and/or flow), upstream of the injection point of the sample to be analyzed; means to process said data detecting the variations caused by the presence of said sample; and means to perform said function or functions. The invention will be now described more in detail with reference to the accompanying drawings, attached for illustrative and not limitative purposes.

BRIEF DECRIPTION OF THE DRAWINGS

DESCRIPTION OF THE PREFERRED EMBODIMENTS

Figure 1:
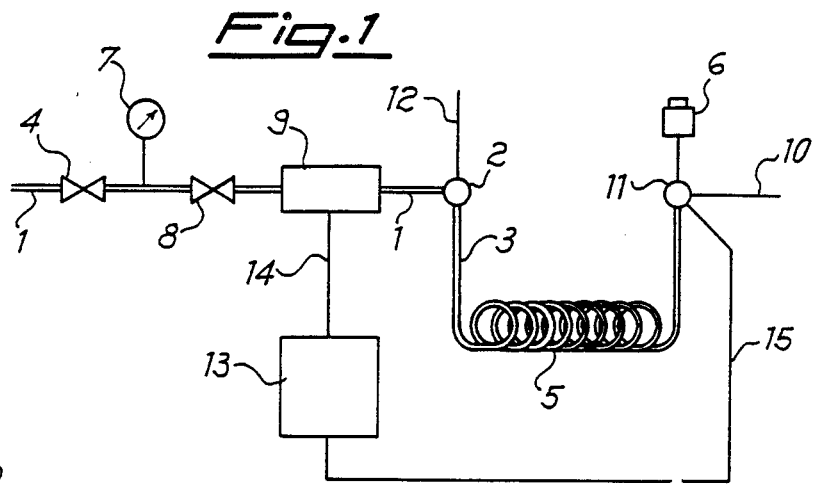
FIG. 1 is a schematic diagram of a first embodiment according to the invention.
Figure 3:
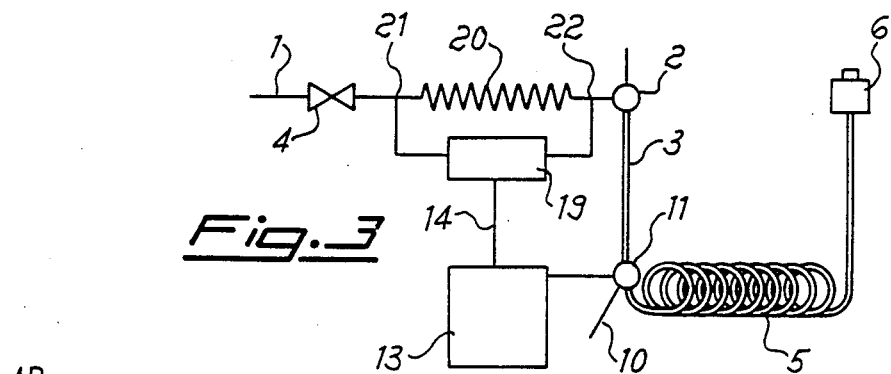
FIG. 3 is a schematic diagram of an embodiment according to the invention, alternative to the embodiment of FIG. 1.

As previously mentioned, the examples in FIGS. 1 and 3 relate to a gas chromatographic equipment fitted with splitter, specially designed for the analysis of samples containing large volumes of solvent such as those consisting of fractions obtained via HPLC (high pressure liquid chromatography). Nevertheless it is obvious that the device according to the invention can be used on any other chromatographic equipment, to which the principle of the invention can be applied, independently from the type of eluent used, from the type of activated function and, in the case of activation of a splitter, from the splitter position along the elution run between injector and detector.

Said principle is based on the fact that the evaporation of the eluent and/or low-boiling components of the sample generates a vapour pressure which on its turn causes variations in the feeding conditions of the inert gas constituting the mobile phase, namely the so-called "carrier". The embodiments of FIGS. 1 and 3 are two examples of a device, designed in function of the different entity of the variations of said carrier conditions.

Referring to FIG. 1, the shown equipment has a feeding line for carrier 1 connected via a valve 2 to a precolumn 3. On its turn the precolumn 3 is connected to a separation column 5, which leads to a detector 6. Along the terminal section of the separation column 5 there is an exhaust duct, or splitter, 10 connected to the separation column 5 by means of a valve 11.

On the carrier feeding duct there are provided, in the opposite direction to the gas flow, starting from the valve 2, a pressure sensor 9, a flow regulator 8, a manometer 7 and a pressure regulator 4; the carrier gas will then flow through said devices 4, 7, 8, 9 before reaching the valve 2 and then the precolumn 3.

The valve 2 also connects the sample feeding duct 12 to the precolumn 3; for instance, according to the type of sample injection used, the valve 2 will constitute an interface of the so-called "loop" type or an interface of the so-called "on-column" type.

The pressure sensor 9 is connected, via a line 14, to a processing unit 13 which on its turn is connected to the valve 11 via a line 15.

The device according to the invention, namely the group consisting of the apparatuses indicated by 9, 13, 14 and 15 can be indifferently used with both types of interfacing valves.

Once again it is hereby underlined that, besides the control of the switching valve of the splitter 11, the device according to the invention can be equally used to control any other functions of the gas chromatograph which depend on the advancement stage of the analysis, that is which are related to the time elapsed from the beginning of the analysis. Furthermore it must be stressed that, being the following description referred to a combined equipment HPLCgas chromatograph, the term "solvent" is intended in its true meaning, but that the concepts described hereunder can be applied to any type of eluent, as for instance to a supercritical fluid.

When the sample is injected into the precolumn 3 via the interface valve 2, the solvent coming into contact with the heated precolumn evaporates and generates a vapour pressure which opposes the passage of the carrier and even tends to push the sample backward. This phenomenon occurs both using the on-column technique and the "loop" interface, and in the last case it is particularly important.

The flow regulator 8 tries to keep the carrier flow constant and therefore (also to avoid that the sample is pushed backward along the precolumn 3) provides to raise the carrier pressure; said increase in any case cannot exceed a predetermined value previously set on the pressure regulator 4.

This variation of the carrier pressure upstream the sample injection point, namely upstream the interface valve 2, is detected by the pressure sensor 9 which transmits the detected data to the processing unit 13 through the line 14. As previously mentioned, the processing unit 13 is on its turn connected to the valve 11 through a second connecting line 15.

When the solvent evaporation is over, the vapour pressure of the solvent disappears and the flow regulator 8, detecting said disappearance, makes the carrier pressure decrease down to the value present before the sample injection. In this case, too, the pressure sensor 9 records a variation in the pressure value and sends it to the processing unit 13.

Figure 2:
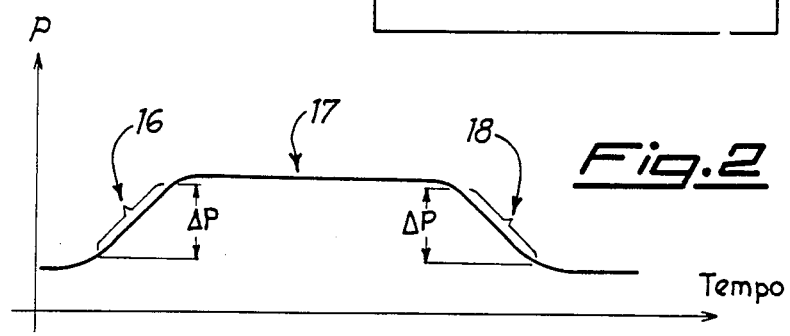
FIG. 2 is a graph showing the variations of a parameter of the carrier feeding in the device of FIG. 1.

The variations of the relative pressure values in the carrier feeding duct 1 are illustrated in the graph of FIG. 2, where the values of the carrier pressure are plotted on the ordinates, while the time elapsed from the the beginning of sample injection is plotted on the abscissae. As it can be noted, pressure P undergoes a first variation with a positive P in the graph area indicated by 16. Said area and said P correspond to the rise of carrier pressure in the duct 1 as effected by the flow regulator 8 because of the vapour pressure generated by the solvent evaporation in the precolumn 3. The subsequent analytical stage, i.e. the time necessary for the solvent to completely evaporate, is represented by the constant pressure plateau present in the graph central area and generically indicated by 17. At the end of the solvent evaporation, a decrease of the carrier pressure in the duct 1 will take place, said decrease being controlled by the flow regulator 8. The P in this case is negative and indicated by reference 18.

It has been noticed that, as soon as the pressure variation with negative P 18 is detected, no condensed solvent is present in the precolumn 3. Generally at the end of the negative pressure variation 18, almost all solvent vapours have been exhausted through the splitter 10 and the processing unit 13 can give the order to switch the valve 11 to a position connecting the separation column 5 to the detector 6. Said order can be given immediately after detecting the negative P 18 or after a subsequent, predetermined, time interval to allow all the solvent still possibly present in the column 5 to be eliminated through the splitter 10. It must be outlined that said pressure variations take place independently from the volume of injected sample and/or eluent; in particular, though the P can vary in width, the speed of pressure variation (that is the graph slope in points 16 and 18) is essentially the same for a wide range of volumes of injected sample. Preferably said interval is determined experimentally in advance. During the analysis of a generic sample containing an eluent giving way to a cycle of variations of carrier pressure similar to that of figure 2, in order to avoid possible errors, the order to switch the valve 11 is given by the processing unit 13 only after the latter has received from the pressure sensor 9 a complete series of pressure values corresponding to variations similar to those illustrated in the graph of FIG. 2. Said variations must substantially involve a pressure increase at the beginning corresponding to the variation in positive 16, a period of constant pressure corresponding to the plateau 17 and a pressure decrease at the end corresponding to the area 18 of the graph of figure 2. Obviously, as already mentioned, positive and negative pressure variations must take place within a determined time period, which means that the graph of said variations must show slopes similar to the ones indicated by references 16 and 18 in FIG. 2. On the contrary, the plateau 17 can have any value, in that the realization of the functions only depends on the graph trend and is independent from the time needed for the eluent complete evaporation.

In the gas chromatograph of FIG. 1 the splitter 10 and the switching valve 11 are fitted to the end portion of column 5, immediately upstream the detector 6; gas chromatographs for analysis of samples with large volumes of solvent are however known, wherein the splitter 10 and valve 11 are fitted to the end of the precolumn 3, immediately upstream of the separation column 5, or between two different separation columns. This arrangement is designed to speed up the analysis time avoiding that the large mass of solvent vapour is forced to elute through the whole column 5 before being exhausted through the splitter 10.

In this case a very large exhaust opening is provided immediately downstream the solvent evaporation area; said disposition involves as a consequence the fact that pressure variations taking place in the feeding duct 1 are smaller and quicker than the previous ones and are generally too small and too quick to be accurately and easily detected b the pressure sensor fitted to the feeding duct 1. Similarly, there are cases where the solvent vapours, for quality or quantity, are not able to generate variations of flow, and therefore of the carrier pressure, having sufficient intensity and/or duration to be satisfactorily measured by the pressure sensor 9. It has been ascertained that the best method to overcome this inconvenience is to measure the variations of the carrier flow instead of the pressure variations as in the case of FIG. 1. For this purpose a modified version of the device according to the invention is used, as shown in FIG. 3.

As it can be noticed in said figure the device according to the invention comprises herein, besides a processing unit 13 connected to the switching valve 11 in a completely similar way to that previously shown in FIG. 1, a flow sensor as well. In the preferred embodiment of FIG. 3, said flow sensor consists of a differential pressure sensor 19 detecting the differential pressure at the two ends of a restrictor 20 mounted in series on the carrier feeding duct 1. Unlike the example of FIG. 1, in this case the carrier feeding pressure is kept constant at the value set in advance on the pressure regulator 4.

The carrier pressure and the restrictor 20 are selected in such a way that the pressure difference, or P, between its upstream end 21 and its downstrean end, indicated by 22, is sufficiently low as to be annulled or reduced significantly by even the least vapour pressure of the solvent which is present in the precolumn 3 immediately after injection. The P variation in function of the time passed from the beginning of the analysis is shown in FIG. 4.

As it can be noticed, in this case the graph trend is substantially reversed with respect to the one shown in FIG. 2. In fact, the formation of vapour pressure in the precolumn 3 causes a reduction in the difference of pressure between the ends 21 and 22 of the restrictor. Said negative variation is indicated by 25 in the graph of FIG. 4.

Figure 4:
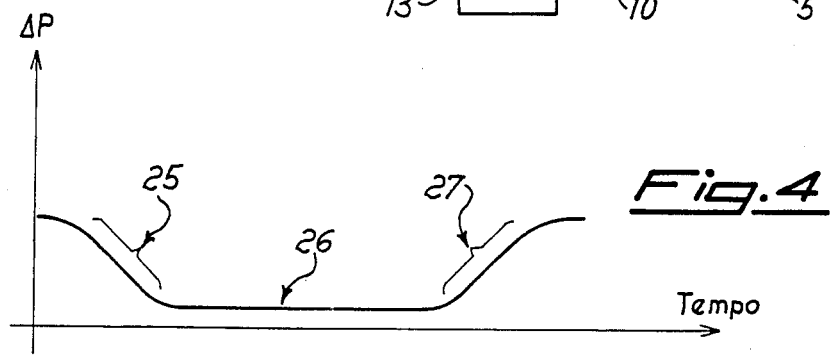
FIG. 4 is a graph of the variations of a parameter of the carrier feeding in the embodiment of FIG. 3.

During the whole period in which solvent vapour is present in the precolumn 3, the flow, namely the difference of pressure between the points 21 and 22 of the restrictor, remains at a constant value which is nil or in any case near to zero; said constant value forms a plateau indicated by 26 in FIG. 4. At the end of the solvent evaporation the flow increases again until it goes back to the initial value corresponding to the difference of pressure before the sample injection into the precolumn 3; said positive variation of the differential pressure is indicated by 27 in the graph of FIG. 4.

It has been verified that, when the positive flow variation occurs, that is when the P value goes back to the initial value, condensed solvent is no longer present inside the precolumn and generally almost all solvent vapours have been at this point exhausted through the splitter 10.

During operation, the flow sensor, or differential pressure sensor 19, records the variations of the difference of pressure between the two ends 21 and 22 of the restrictor 20 and transmits them via the line 14 to the aforementioned processing unit 13. The unit 13 on its turn processes said data to switch the valve 11 from a position connecting the precolumn 3 to the splitter 10 to a position connecting the precolumn 3 to the separation column 5. Similarly to what described for the method relating to the apparatus of FIG. 1, the commutation control will be given when the unit 13 has verified that the differential pressure variation (or flow variation) has followed a trend similar to that shown in FIG. 4; in this case as well the differential pressure variations have to take place in well determined time intervals, i.e. the graph resulting from said variations must have variations with a slope similar to the one indicated by 25 and 27 in the graph of FIG. 4.

Figure 5:
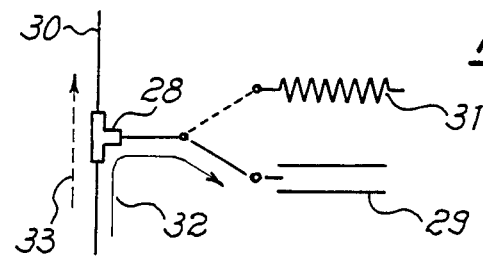
FIG. 5 is a scheme of a preferred embodiment of a splitter valve.

In the embodiments shown in FIGS. 1 and 3, a splitter was shown, wherein a generic valve 11, actuated by the processing unit 13, does or does not run the eluent flow to the exhaust 10. FIG. 5 shows a type of splitter which can be advantageously used in the gas chromatographic equipment comprising the device according to the invention. Said splitter has been described in principle by Pacciarelli et al. (Proceedings 8th Int. Symp. on Capillary Chromatography, Riva del Garda, 1987, Huthig, Heidelberg, page 1204) and essentially consists of a "T" fitting 28 located along the normal duct 30 of gases elution and optionally connectable either to an exhaust 29 having a much greater internal diameter than that of duct 30 (and therefore a much lower hydraulic resistance), or to an exhaust 31 having a much lower internal diameter than that of duct 30 and therefore a higher hydraulic resistance.

Figure 6:
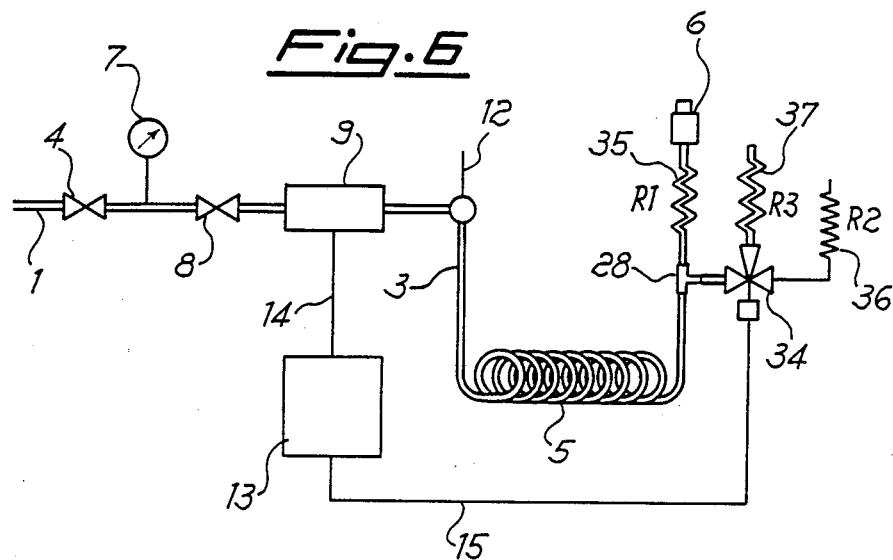
FIG. 6 is a schematic diagram of the device of FIG. 1 utilizing the valve of FIG. 5.

Connecting the "T" 28 to the exhaust 29, most of what elutes along the duct 30 is deviated towards the reduced resistance exhaust 29, following the run indicated by arrow 32. On the contrary connecting the "T" 28 to the exhaust 31, most of the eluent continues to flow along the duct 30 following the run indicated by the broken arrow 33, while only a small portion is eluted through the high resistance exhaust 31. FIG. 6 shows the application of a valve of the aforedescribed type to a gas chromatographic equipment of the type described with reference to FIG. 1.

As it can be noticed, at the downstream end of the separation column 5 a "T" fitting 28 is provided connecting the column 5 to a terminal duct 35 which, due to its internal diameter, will form a first resistance R1. The "T" fitting 28 is in turn connected to a three-way electrovalve 34 (connected to the processing unit 13 via the line 15), from which two exhaust ducts 36 and 37 come out. In particular the duct 36 will have a much lower internal diameter than both duct 37 and duct 35, while the duct 37 has an internal diameter which is much higher than that of the ducts 35 and 36.

If R2 is the hydraulic resistance offered to eluent run by duct 36 and R3 the one provided by duct 37, it will result that $R2 > R1 > R3$.

Consequently, by appropriately switching the electrovalve 34 thanks to the signals sent by the processing unit 13, it is possible to guide the eluent flow through the exhaust with less resistance 37 or along the terminal duct 35 up to the detector 6. It is herein pointed out that the eluent always flows in any case through the duct 35, even if with different flowrates according to the position selected for the electrovalve 34.

Figure 7:
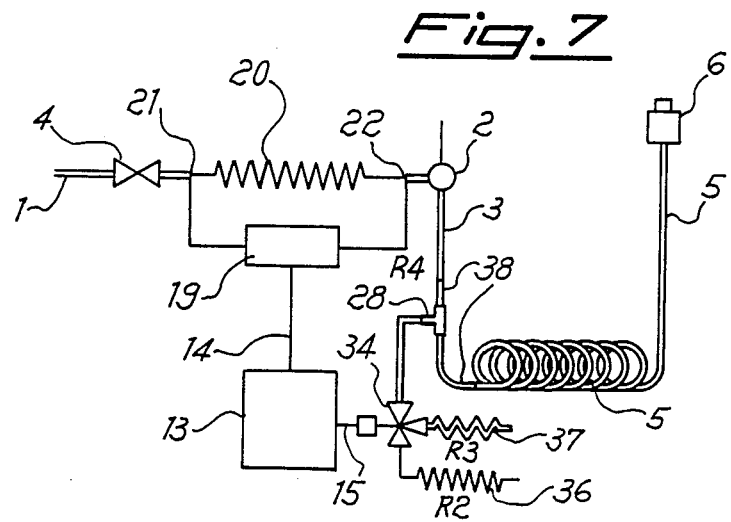
FIG. 7 is a schematic diagram of the device of FIG. 3 utilizing the valve of FIG. 5.

A similar arrangement can be used also in the apparatus described in FIG. 3. Said arrangement is illustrated in FIG. 7, where the same reference numberals of FIG. 6 are used for corresponding parts.

As it can be noticed, in this case too there is provided a three-way electrovalve 34 connected to and worked by the processing unit 13 via the line 15. The electrovalve 34 is fitted onto a duct 38, which connects the precolumn 3 to the separation column 5, by means of a "T" 28. The electrovalve 31 is connected to an exhaust opening 37 with large internal diameter and small resistance and to an exhaust opening 36 with small internal diameter and high resistance. In particular, the internal diameter of exhaust 37 will be much greater than both the one of exhaust 36 and the one of duct 38, while the internal diameter of exhaust 36 will be much lower than both the one of duct 38 and (as already mentioned) the one of exhaust 37.

Indicating by R4 the hydraulic resistance of the duct 38 and by R2 and R3 those of the exhausts 36 and 37 respectively, it will result R2>R4>R3.

Similarly to what described hereinabove, by appropriately switching the valve 34 via the signals coming from unit 13, the eluent will be mostly discharged through the exhaust duct 37 or sent to the separation column 5, according to the switching controlled by the unit 13 on the basis of the signals coming from sensor 19.

In the preceding examples the hydraulic resistance offered by the ducts 36 and 37 depended on the diameter of the the ducts themselves, however said resistance can be varied in function of other parameters, such as the duct length or the pressure value inside or at the outlet of said ducts.

Figure 8:
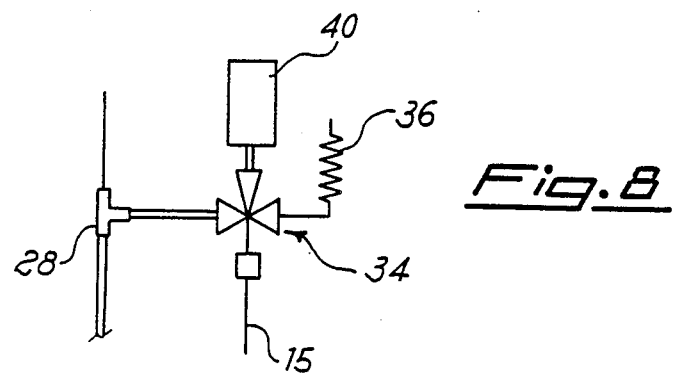
FIGS. 8 to 10 are diagrams of possible alternative embodiments of the splitter valve.
Figure 9:
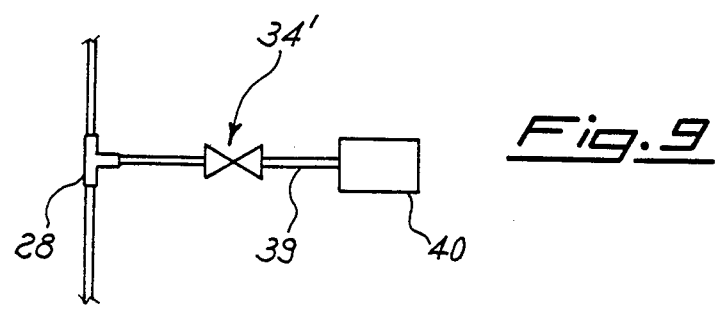
Figure 10:
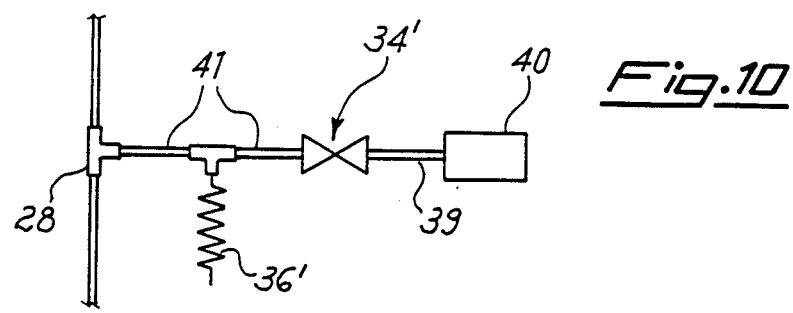

FIGS. 8, 9 and 10 illustrate three particular embodiments of splitter where the duct 37 with reduced resistance has been replaced by a source of reduced pressure 40. Said source, which can be connected to an outlet of the valve 34, directly or via a duct 39, does not only zerosets the relevant hydraulic resistance, but has also the function of speeding up evaporation of the eluent present in the column or precolumn.

The embodiment of FIG. 8 is quite similar to the splitter shown in FIGS. 6 and 7, with the aforementioned modification consisting in the presence of a vacuum source 40. FIG. 9 illustrates a modification of the splitter of FIG. 8, wherein the electrovalve 34' is no more a threeway one but a twoway valve, one of its outlets being connected to the vacuum source 40 and the other to the "T" fitting 28. In fact the presence of the reduced pressure source 40 makes the outlet with the duct 36 at resistance R2 practically needless, in that the vacuum almost completely eliminates any trace of eluent from the valve 34', making its flowing back to the "T" 28 very unlikely.

However, to be thoroughly sure, the embodiment shown in FIG. 10 can be adopted, wherein the electrovalve 34' is still a twoway one, but a duct 36' with very reduced diameter and high resistance is provided on the duct 41 which connects the electrovalve 34' to the "T" fitting 28.

As previously mentioned, the aforereported examples exclusively concern the control of the switching valve of a splitter in a gas chromatograph during the analysis of samples with large volumes of solvent; it is however evident that the device according to the present invention can be used also to control the other functions of the gas chromatograph which depend on the advancement stage of the analysis.

In particular the device according to the invention enables to detect the variations caused by the presence or absence of the sample in the injection area and to use said variations just to regulate those functions.

For instance the device according to the invention can be used to set up the beginning of a temperature program with resulting increase of the analytical temperature at the end of the solvent evaporation, independently from the fact that said solvent is eventually eliminated through a splitter or not.

Similarly, the device according to the present invention can be used to operate the injection valve, for instance to switch it to the position previous to sample injection as soon as the desired variation of pressure and/or flow of the eluting gas takes place.

I claim:

1. A method for detecting quantitative variations in the passage of a fluid sample comprising solvent and eluent through a column or precolumn of a gas chromatograph having a plurality of functions in order to control at least one of said functions, said method comprising:
   introducing said fluid sample at a fluid sample introduction point upstream of said precolumn, which precolumn is upstream of said column;
   feeding a carrier gas at a carrier gas feeding point upstream of said fluid sample introduction point so that said carrier gas carries said fluid sample in a downstream direction through said precolumn and said column;
   heating said fluid sample in said precolumn so that at least said solvent vaporizes;
   detecting variations of the pressure or flow of said carrier gas upstream of said fluid sample introduction point; and
   controlling at least one of said plurality of functions of said gas chromatograph in response to said detected variations.

2. The method of claim 1, wherein variations in said pressure of said carrier gas are detected.

3. The method of claim 2, wherein said detecting of variations of said carrier gas pressure comprises detecting a positive pressure variation having a value and duration within a predetermined range, a period of substantially constant pressure, and a negative pressure variation having a value and duration within a predetermined range, and said controlling of said at least one of said plurality of functions comprises controlling at least one function correlated to the presence of said eluent in said column or precolumn.

4. The method of claim 3, wherein said chromatograph comprises an exhaust duct and a valve means for changing the direction of said sample flow from said downstream direction to said exhaust duct, said valve means and said exhaust duct being located downstream of said precolumn, and said controlling of at least one of said plurality of functions correlated to the presence of eluent comprises switching said valve means to change said sample flow direction between said downstream direction and said exhaust duct in response to said predetermined pattern of said detected variations.

5. The method of claim 1, wherein variations in the flow of said carrier gas are detected.

6. The method of claim 5, wherein said detecting of variations of carrier gas flow comprises detecting a positive pressure variation having a value and duration within a predetermined range, a period of substantially constant flow, and a negative flow variation having a value and duration within a predetermined range, and said controlling of said at least one of said plurality of functions comprises controlling at least one function correlated to the presence of said eluent in said column or precolumn.

7. An apparatus for controlling at least one function of a gas chromatograph having a plurality of functions, said gas chromatograph comprising a column, a precolumn upstream of said column, fluid sample introduction means for introducing a fluid sample comprising solvent and eluent upstream of said precolumn, and carrier gas feeding means for feeding a carrier gas at a point upstream of said fluid sample introduction means so that said carrier gas carries said fluid sample in a downstream direction through said precolumn and said column, said apparatus comprising:

means for detecting variations in the pressure or flow of said carrier gas upstream of said fluid sample introduction means; and means for controlling at least one of said plurality of functions of said gas chromatograph in response to said detected variations.

8. The apparatus of claim 7, wherein said carrier gas feeding means comprises a carrier gas feeding duct and said means for detecting pressure or flow variations comprises a flow sensor fitted to said carrier gas feeding duct.

9. The apparatus of claim 8, wherein said flow sensor comprises means for restricting the flow of a vapor having a first end and a second end and a sensor for sensing the pressure differential between said first end and said second end of said detecting means.

10. The apparatus of claim 7, wherein said chromatograph further comprises splitter means downstream of said precolumn, said splitter means comprising an exhaust duct, valve means for changing the direction of said sample flow from said downstream direction to said exhaust duct, and means for switching said valve means to change said sample flow direction, and said means for controlling at least one of said plurality of functions actuates said switching means to change said sample flow direction in response to said predetermined pattern of detected variations.

11. The apparatus of claim 10, wherein said valve means for changing the direction of said sample flow comprises a three-way electrovalve comprising a first connection to a first outlet, a second connection to a second outlet and a third connection to a T-fitting located downstream of said precolumn, said second outlet having a hydraulic resistance higher than the hydraulic resistance of said T-fitting, and said T-fitting having a hydraulic resistance higher than the hydraulic resistance of said first outlet, said switching means being actuatable to change said sample flow direction by switching said electrovalve to said first connection so that a substantial portion of said sample flows through said first outlet, or by switching said electrovalve to said second connection so that a substantial portion of said sample flows through said T-fitting in said downstream direction.

12. The apparatus of claim 11, wherein said first outlet is connected to a source of reduced pressure.

13. The apparatus of claim 10, wherein said valve means for changing the direction of said sample flow comprises a two-way electrovalve comprising a first connection to a source of reduced pressure and a second connection to a T-fitting located downstream of said precolumn, said switching means being actuatable to change said sample flow direction by switching said electrovalve to said first connection so that a substantial portion of said sample flows to said source of reduced pressure or by switching said electrovalve to said second connection so that a substantial portion of sample flows through said T-fitting in said downstream direction.

14. The apparatus of claim 13, wherein said two-way electrovalve further comprises an exhaust duct connected to said second connection, said exhaust duct having a hydraulic resistance higher than the hydraulic resistance of said T-fitting, whereby when said valve means is switched to said first connection, there is substantially no backflow of said sample to said T-fitting.

15. The apparatus of claim 7, wherein said means for controlling at least one of said plurality of functions comprise microprocessor means.

16. The apparatus of claim 7, wherein said carrier gas feeding means comprising a carrier gas feeding duct and said means for detecting pressure or flow variation comprises a flow rate regulator and a pressure sensor fitted to said carrier gas feeding duct.

* * * * *